(12) United States Patent
Shindo et al.

(10) Patent No.: US 8,570,495 B2
(45) Date of Patent: Oct. 29, 2013

(54) WHOLE BLOOD IMMUNITY MEASURING DEVICE AND WHOLE BLOOD IMMUNITY MEASURING METHOD

(75) Inventors: Takaaki Shindo, Kyoto (JP); Itsuo Ito, Kyoto (JP)

(73) Assignee: Horiba, Ltd., Kyoto (JP)

( * ) Notice: Subject to any disclaimer, the term of this patent is extended or adjusted under 35 U.S.C. 154(b) by 145 days.

(21) Appl. No.: 13/237,662

(22) Filed: Sep. 20, 2011

(65) Prior Publication Data

US 2012/0075616 A1    Mar. 29, 2012

(30) Foreign Application Priority Data

Sep. 24, 2010 (JP) ................................ 2010-213995
Aug. 31, 2011 (JP) ................................ 2011-189066

(51) Int. Cl.
  *G01N 33/48*   (2006.01)
(52) U.S. Cl.
  USPC .................................. 356/39; 356/40; 356/41
(58) Field of Classification Search
  USPC .......................................................... 356/39
  See application file for complete search history.

(56) References Cited

U.S. PATENT DOCUMENTS 3,743,424 A * 7/1973 Coulter ............................ 356/73

FOREIGN PATENT DOCUMENTS

| EP | 0905514 A1 * | 9/1998 |
| EP | 2 136 210 | 12/1999 |
| EP | 2136210 A1 * | 12/2009 |
| JP | 0 905 514 | 3/1999 |
| JP | 11-101798 | 4/1999 |

OTHER PUBLICATIONS

Nagao, Shunji et al. "Automatic Blood Cell and CRP Counter LC-178 CRP", Horiba Technical Reports, Mar. 1994, pp. 42-47.
"[New Model] Automatic Blood Cell Count/CRP Measuring Apparatus", Horiba, Oct. 6, 2008, 3 pages, www.horiba.com/fr/corporate-news/news/article/new-model-automatic-blood-cell-count-crp-measuring-apparatus-4606/.
European Application No. 11182452.0 Extended European Search Report dated Jan. 23, 2012, 8 pages.

* cited by examiner

*Primary Examiner* — Tarifur Chowdhury
*Assistant Examiner* — Omar Nixon

(57) ABSTRACT

A whole blood immunity measuring device includes a hemolytic reagent supply device that supplies a hemolytic reagent to a whole blood sample, a first light source that irradiates light on a first blood sample as being the whole blood sample to which the hemolytic reagent is added, a first light detection device that detects transmitted first light intensity, and a Hgb calculation part that calculates concentration of hemoglobin based on the first light intensity. An immunoreagent supply device supplies an immunoreagent to the first sample, a whole second light source irradiates light on a second blood sample as being the first sample to which the immunoreagent is added. A second light detection device detects transmitted second light intensity, and a measuring object calculation part that calculates a concentration of the measuring object based on the second light intensity.

6 Claims, 5 Drawing Sheets

WHOLE BLOOD IMMUNITY MEASURING DEVICE AND WHOLE BLOOD IMMUNITY MEASURING METHOD

RELATED APPLICATIONS

The present application claims priority from Japanese Application No. 2010-213995 filed on Sep. 24, 2010 and Japanese Application No. 2011-189066 filed on Aug. 31, 2011.

FIELD OF THE ART

This invention relates to a whole blood immunity measuring device and a whole blood immunity measuring method that measures a concentration of hemoglobin in whole blood and a concentration of a measuring object such as, for example, C-reactive protein (hereinafter also referred to as CRP) in a plasma component.

BACKGROUND ART

As this kind of the whole blood immunity measuring device, as shown in the patent document 1, a whole blood sample and a reagent necessary for each measuremet including a hemolytic reagent are supplied to each of a Hgb cell (corresponds to a WBC cell) to measuer a concentration of hemoglobin and a CRP cell to measure a concentration of CRP so as to prepare samples for each measurement and light is irradiated on each sample, and then each concentration is calculated based on the light intensity of the light transmitting each cell. In this application, the hemolyzed blood indicates a phenomenon of breakdown of a plasma membrane of a red blood cell. In addition, the whole blood sample may be only whole blood or it may contain the whole blood and an anticoagulant or the like.

PRIOR ART DOCUMENT

Patent Document

Patent document 1: Japanese Unexamined Patent Application Publication No. 11-101798

DISCLOSURE OF THE INVENTION

Problems to be Solved by the Invention

However, since the samples for each measurement are prepared respectively, a number of times to supply the samples is increased. In addition, since it is required to clean the nozzle every time the sample is supplied, it becomes difficult to shorten a time for measurement and troublesome to conduct the measurement.

Furthermore, in order to secure the measurement accuracy, it becomes necessary to prepare the samples for each measurement by an amount more than a certain amount respectively. As a result of this, there are problems such that it becomes difficult to reduce a running cost by decreasing the amount of the reagent to be used or to reduce a burden for a human subject whose blood is collected by decreasing an amount of the blood to be collected.

Then the present claimed invention intends to solve all of the problems, and a main object of this invention is to provide a whole blood immunity measuring device that can measure a concentration of hemoglobin and a concentration of a measuring object such as C-reactive protein in whole blood quickly and accurately with reducing a running cost and a burden for a human subject.

Means to Solve the Problems

More specifically the whole blood immunity measuring device in accordance with this invention is characterized by comprising a hemolytic reagent supply device that supplies a hemolytic reagent to a whole blood sample, a first light source that irradiates light on a first sample as being the whole blood sample to which the hemolytic reagent is added, a first light detection device that receives the light emitted from the first light source and transmitting through the first sample and that detects first light intensity as being intensity of the received light, a Hemoglobin (Hgb) calculation part that calculates a hemoglobin concentration in the whole blood sample based on the first light intensity detected by the first light detection device, an immunoreagent supply device that supplies an immunoreagent to the first sample, a second light source that irradiates light on a second sample as being the first sample to which the immunoreagent is added, a second light detection device that receives the light emitted from the second light source and transmitting through the second sample and that detects second light intensity as being intensity of the received light, and a measuring object calculation part that calculates concentration of the measuring object based on the second light intensity in the process of an immune reaction of the measuring object to the immune component in the immunoreagent after the immunoreagent is added by the immunoreagent supply device and the hemoglobin concentration calculated by the Hgb calculation part.

In accordance with this arrangement, since the concentration of hemoglobin is measured by the use of the first sample as being a product of a previous step of the second sample to be used for measuring the measuring object, it is possible to reduce a number of times to supply the reagent and a number of times to clean the nozzle used for supplying the reagent As a result of this, it is possible to shorten the time for measurement and to save a lot of labor. In addition, since there is no need of securing more than a certain amount of the sample for measuring hemoglobin and more than a certain amount of the sample for measuring CRP respectively, it is possible to reduce a necessary amount of the reagent with the measurement accuracy guaranteed so that the running cost can be decreased. In addition, since the amount of the blood to be collected can be decreased, it is also possible to reduce a burden for subject whose blood is collected.

In addition, in case of a conventional device, the blood collecting vessel housing the collected blood is set to the conventional device and the blood collecting vessel can not be taken out until the whole blood is supplied to multiple cells respectively so that there is a problem that an operator has to wait during this period. Contrarily, with the whole blood immunity measuring device of the present claimed invention, it is possible to remove the blood collecting vessel just by collecting the whole blood only once from the blood collecting vessel. Then a waiting period can be reduced by far.

In case that the appropriate cell length for the measurement of the Hgb differs from the appropriate cell length for the measurement of the measuring object, it is preferable that a first cell, a second cell arranged separately from the first cell and a transport device that transports the sample between the first cell and the second cell are further comprised, and the first light source irradiates the light on the first sample transported to the second cell from the first cell by the transport device, the immunoreagent supply device supplies the immunoreagent to the first sample returned from the second cell to the first cell by the transport device, and the second light source irradiates the light on the second sample housed in the first cell.

In addition, if the dilution ratio of the sample appropriate for the preceding measurement is bigger than the dilution ratio of the sample appropriate for the subsequent measurement, it is not possible to use the sample for both measurements. Then it is preferable to use the sample in a concentrated state without dilution in a step of measuring Hgb as being the preceding measurement. In order to make it possible to conduct the measurement with high accuracy even though the sample is in a condensed state, it can be conceived that a cell length is shortened in view of the absorbency. However, there is a problem that bubbles likely remain in the cell just by shortening the cell length. In order to solve this problem, it is preferable that an internal flow channel formed inside of the second cell is in a shape of getting thicker smoothly and gradually from an introducing port from which the sample is introduced and a lead-out port from which the sample is lead out headed to a center part viewed from an optical axis direction of the light from the first light source.

In order to discharge the bubbles more effectively, it is preferable that a width in a direction orthogonal both to the direction of the flow of the sample and to a direction of an optical axis of the light from the first light source in the center part of the internal flow channel of the second cell is 1.2~2.0 times as long as a width in the orthogonal direction in the introducing port and the lead-out port.

As an example of the measuring object whose concentration can be measured accurately in case that the whole blood immunity measurig device conducts the immunity measurement represented is the measuring object is C-reactive protein.

A whole blood immunity measuring method used for the whole blood immunity measuring device is also one of the present claimed inventions. More specifically, the whole blood immunity measuring method in accordance with this invention is a method comprising a first sample preparation step that prepares a first sample by adding a hemolytic reagent to whole blood, a first light intensity measuring step that irradiates light on the first sample and measures a first light intensity as being an intensity of light transmitting the first sample, a Hgb calculation step that calculates a concentration of hemoglobin in the whole blood based on the first light intensity, an immune reaction occurrence step that adds the immunoreagent to the first sample and causes an immune reaction of a measuring object in the first sample to an immune component in the immunoreagent, a second light intensity measuring step that irradiates light on the second sample as being a first sample to which the immunoreagent is added and measures the second light intensity as being the intensity of the light transmitting the second sample in the process of an immune reaction of the measuring object to the immune component, and a measuring object calculating step that calculates a concentration of the measuring object based on the second light intensity and the hemoglobin concentration.

Effect of the Invention

In accordance with the invention, it is possible to measure the concentration of hemoglobin and the concentration of the measuring object in whole blood quickly and accurately with a simple operation by reducing a running cost and a burden for subject.

BEST MODES OF EMBODYING THE INVENTION

Figure 1:
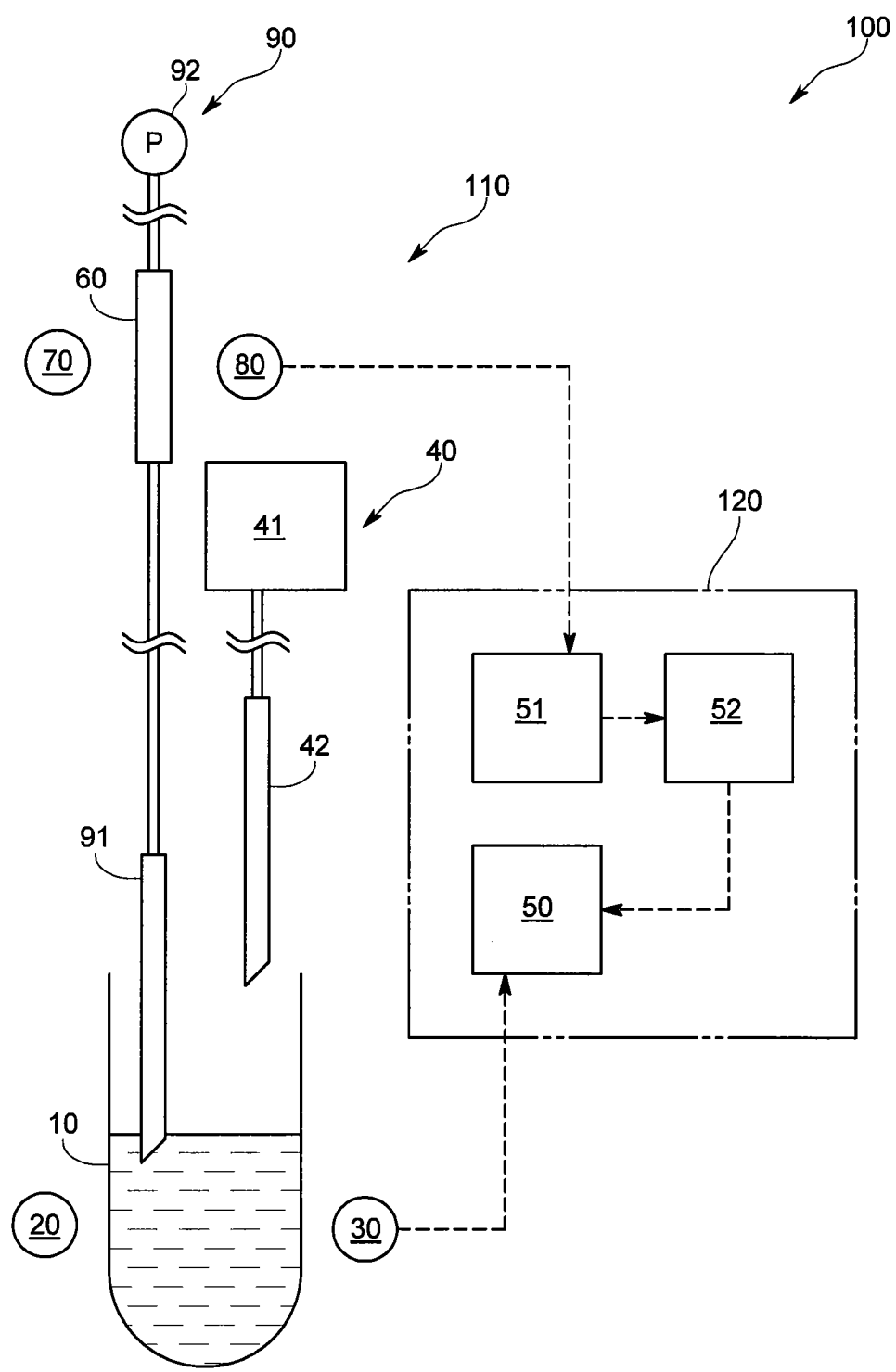
FIG. 1 is a pattern device configuration diagram of a whole blood immunity measuring device in accordance with one embodiment of this invention.

A whole blood immunity measuring device 100 in accordance with one embodiment of this invention will be explained with reference to drawings. The whole blood immunity measuring device 100 measures a concentration of hemoglobin in whole blood and a concentration of C-reactive protein as being a measuring object in plasma component by the use of the whole blood sample as being human blood or animal blood. Concretely, the whole blood immunity measuring device 100 comprises, as shown in FIG. 1, a measuring mechanism 110 and a calculation mechanism 120 that conducts calculation in accordance with the measuring mechanism 110.

The measuring mechanism 110 comprises a first cell 10 that houses a sample, a second light source 20 that irradiates light on the sample housed in the first cell 10, a second light detection device 30 that receives the light irradiated from the second light source 20 and transmitting the sample and detects the second light intensity as being the intensity of the received light, and a reagent supply device 40 (corresponds to the hemolytic reagent supply device and the immunoreagent supply device in claims) that supplies the reagent to the first cell 10.

Each part will be described in detail. The first cell 10 is in a shape of a pipe having a bottom and inside of which formed is an internal space to house the sample. The first cell is generally in a channel shape or a "V" shape viewed from an optical axis direction of the light from the second light source 20 and a discharge port (not shown in drawings) to discharge the sample is arranged on a center part of the bottom part. In addition, an incidence window to which the light is incident in the internal space faces in parallel to an exit window from which the light exits. A previously deteremined amount of the whole blood is supplied to the first cell 10 from a blood collecting vessel (not shown in drawings) that houses the whole blood sample by a whole blood sample collecting nozzle (not shown in drawings).

The second light source 20 is arranged to face the first cell 10, and is LEDs that irradiate the light whose peak wavelength is more than or equal to 600 nm. The peak wavelength of the second light source 20 in this embodiment is 660 nm.

The second light detection device 30 is arranged to face the second light source 20 and is a photodiode in this embodiment.

The reagent supply device 40 comprises a reagent vessel 41 that houses a hemolytic reagent, a buffer reagent and an immunoreagent, a reagent supply nozzle 42 that supplies each of the above-mentioned reagents to the first cell 10 and a solenoid valve (not shown in drawings) that adjusts an open degree of a valve disk so as to pass each reagent through the reagent supply nozzle 42 by a predetermined amount. The reagent supply device 40 prepares the first sample by adding the hemolytic reagent (for example, a hemolytic saponin reagent) to the whole blood sample housed in the first cell 10. In addition, the reagent supply device 40 prepares the second sample by adding the buffer reagent to the first sample so as to adjust the pH and diluting the first sample to a previously determined dilution ratio and furthermore adding the immunoreagent (for example, CRP-X2 (DENKA SEIKEN CO., LTD.)) to the diluted first sample. The immunoreagent includes an immunity component (including latex of an anti-CRP antibody sensitivity) that agglutinates due to an immune reaction to the CRP in the first sample.

The calculation mechanism 120 is a dedicated or a general purpose computer, and stores predetermined programs in a memory and cooperatively operates a CPU and its peripheral devices based on the programs so as to produce a function as a CRP calculation part 50 corresponding to the measuring object calculation part in claims. The CRP calculation part 50 calculates the concentration of CRP in the plasma component based on the time change amount of the second light intensity in a process of agglutination due to the immune reaction of the CRP to the immunity component in the immunoreagent after the immunoreagent is added by the reagent supply device 40 and the concentration of hemoglobin, to be described later.

Furthermore, in this embodiment, the measuring mechanism 110 comprises a second cell 60 arranged separately from the first cell 10, the first light source 70 that irradiates light on the sample housed in the second cell 60, the first light detection device 80 that receives the light irradiated from the first light source 70 and transmitting the sample and that detects the first light intensity as being the intensity of the received light, and a transport device 90 that transports the sample between the first cell 10 and the second cell 60.

Figure 2:
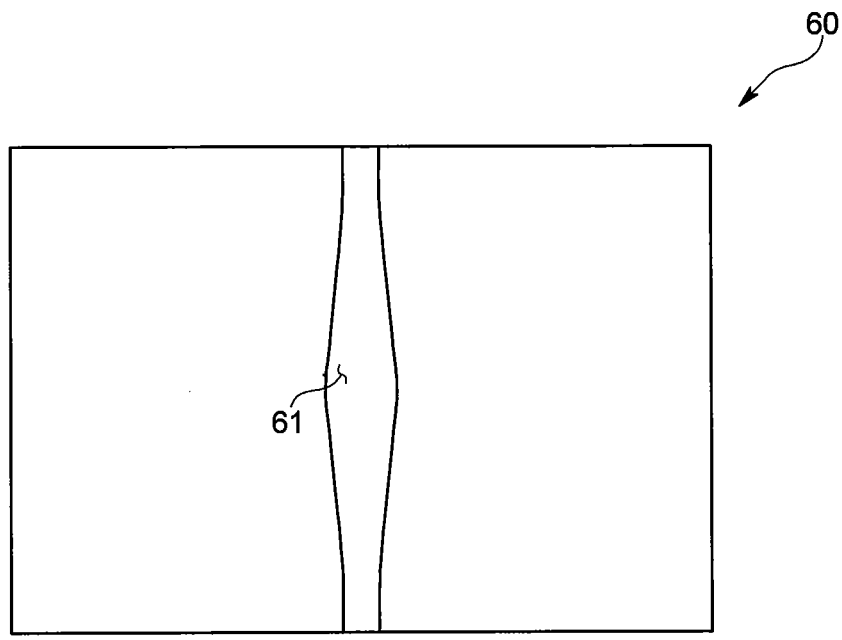
FIG. 2 is a front view and a perspective view of a second cell of the whole blood immunity measuring device in accordance with this embodiment.
Figure 2:
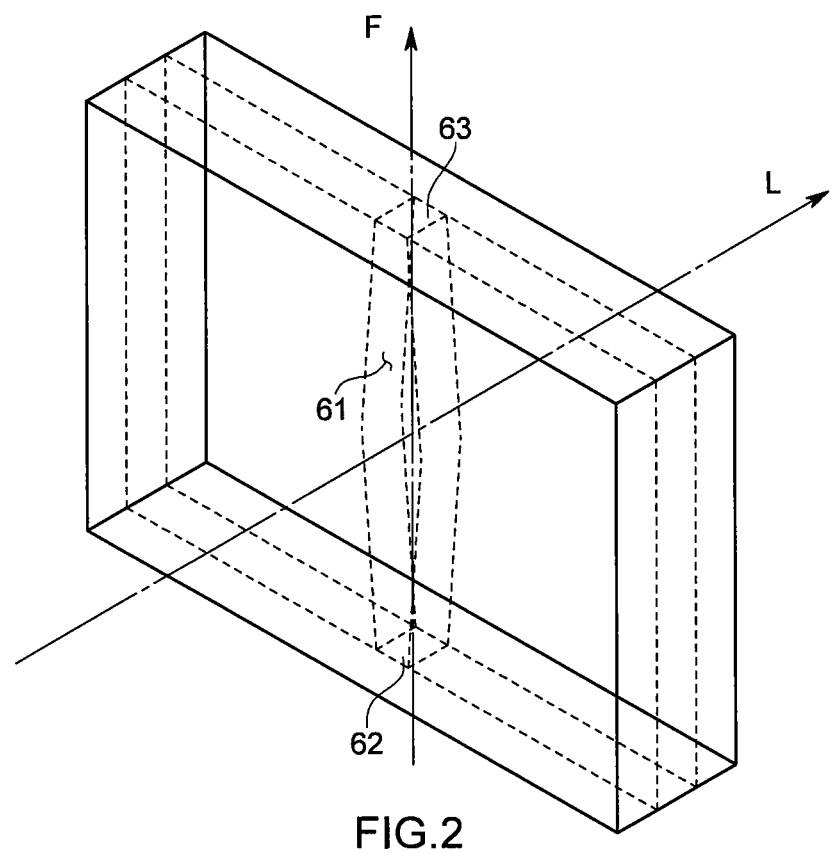

The second cell 60 is, as shown in FIG. 2, a cell of a flow cell type inside of which formed is an internal flow channel 61 where the sample flows. The internal flow channel 61 is in a fusiform shape of getting thicker smoothly and gradually from an introducing port 62 from which the sample is introduced and a lead-out port 63 from which the sample is lead out headed to a center part viewed from an optical axis direction (L) of the light from the first light source 70. A width (1.5 mm in this emodiment) in the orthogonal direction as being a direction orthogonal both to the flowing direction (F) of the sample and to the optical axis direction (L) of the light from the first light source 70 in the center part of the internal flow channel 61 of the second cell 60 is 1.2~2.0 times as long as a width in the orthogonal direction in the introducing port 62 and the lead-out port 63, and in this embodiment the width in the orthogonal direction is set to be 1.5 times.

In the internal flow channel 61, the incidence window to which the light is incident and the exit window from which the light exits face each other in parallel, and a cell length as being a distance between the incidence window and the exit window in the optical axis direction (L) is less than 1 cm, and in this embodiment the cell length is set to be 1 mm.

The first light source 70 is, as shown in FIG. 1, arranged to face the second cell 60, and is LEDs that irradiate the light whose peak wavelength is 500~550 nm. The peak wavelength of the first light source 70 in this embodiment is 510 nm.

The first light detection device 80 is arranged to face the first light source 70 with the second cell 60 arranged therebetween and is a photodiode in this embodiment.

The transport device 90 comprises a transport pipe 91 and a pump 92, and one end of the transport pipe 91 is connected to the introducing port 62 of the second cell 60, and one end of a pipe mounted on the pump 92 is connected to the lead-out port 63 of the second cell 60. When inside of the pump 92 is depressurized with the other end of the transport pipe 91 immersed in the sample housed in the first cell 10, the sample is transported from the first cell 10 to the second cell 60 through the transport pipe 91. In order to return the sample from the second cell 60 to the first cell 10, inside of the pump 92 is pressurized.

In addition, the calculation mechanism 120 has functions as a Hgb calculation part 51 and a Hct conversion part 52. The Hgb calculation part 51 calculates the concentration of hemoglobin in the whole blood based on the first light intensity detected by the first detection device 80. The Hct conversion part 52 converts the concentration of hemoglobin in the whole blood calculated by the Hgb calculation part 51 into the hematocrit by the use of a predetermined conversion formula.

Figure 3:
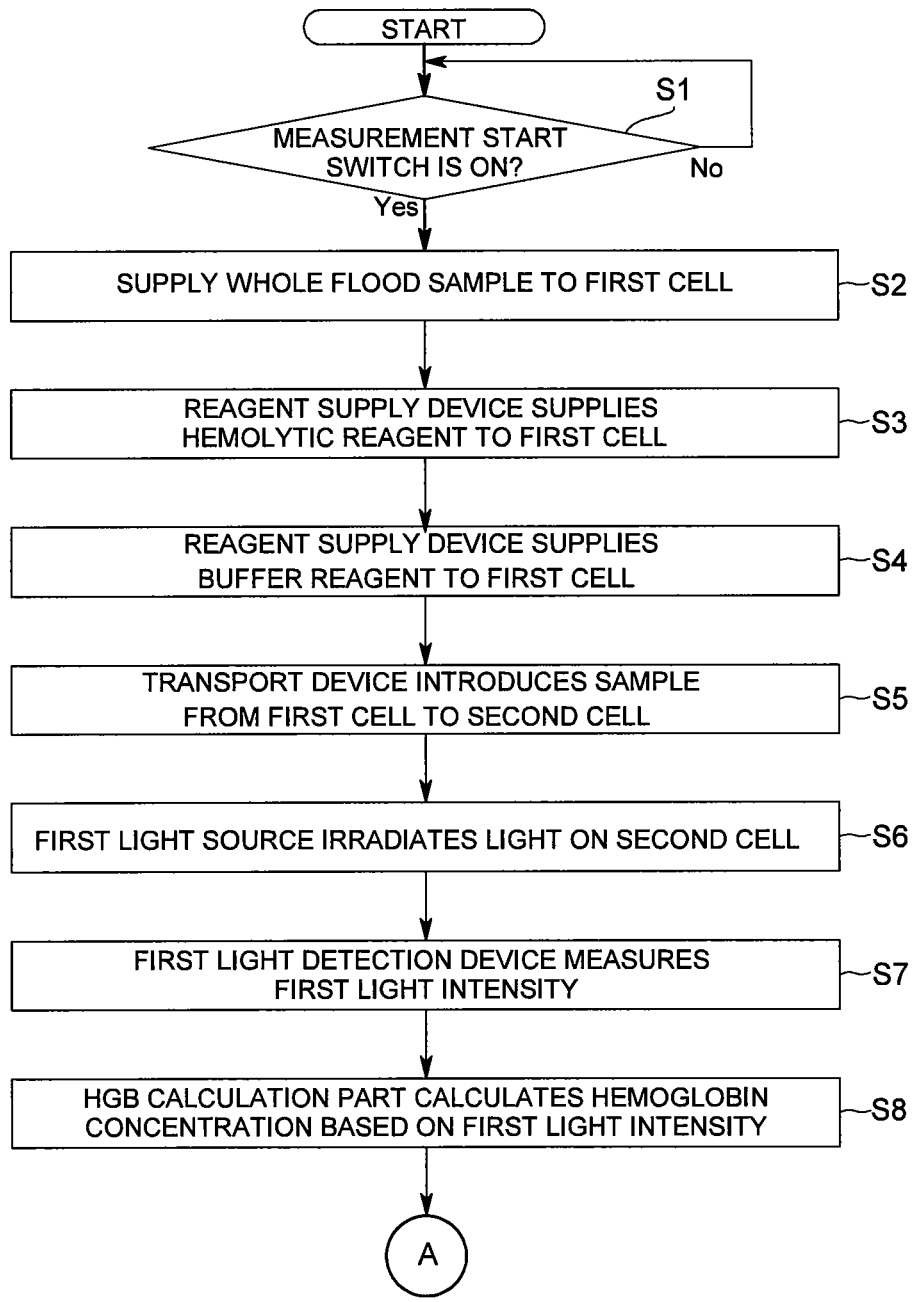
FIG. 3 is a flow chart showing an operation procedure of the whole blood immunity measuring device in accordance with this embodiment.
Figure 4:
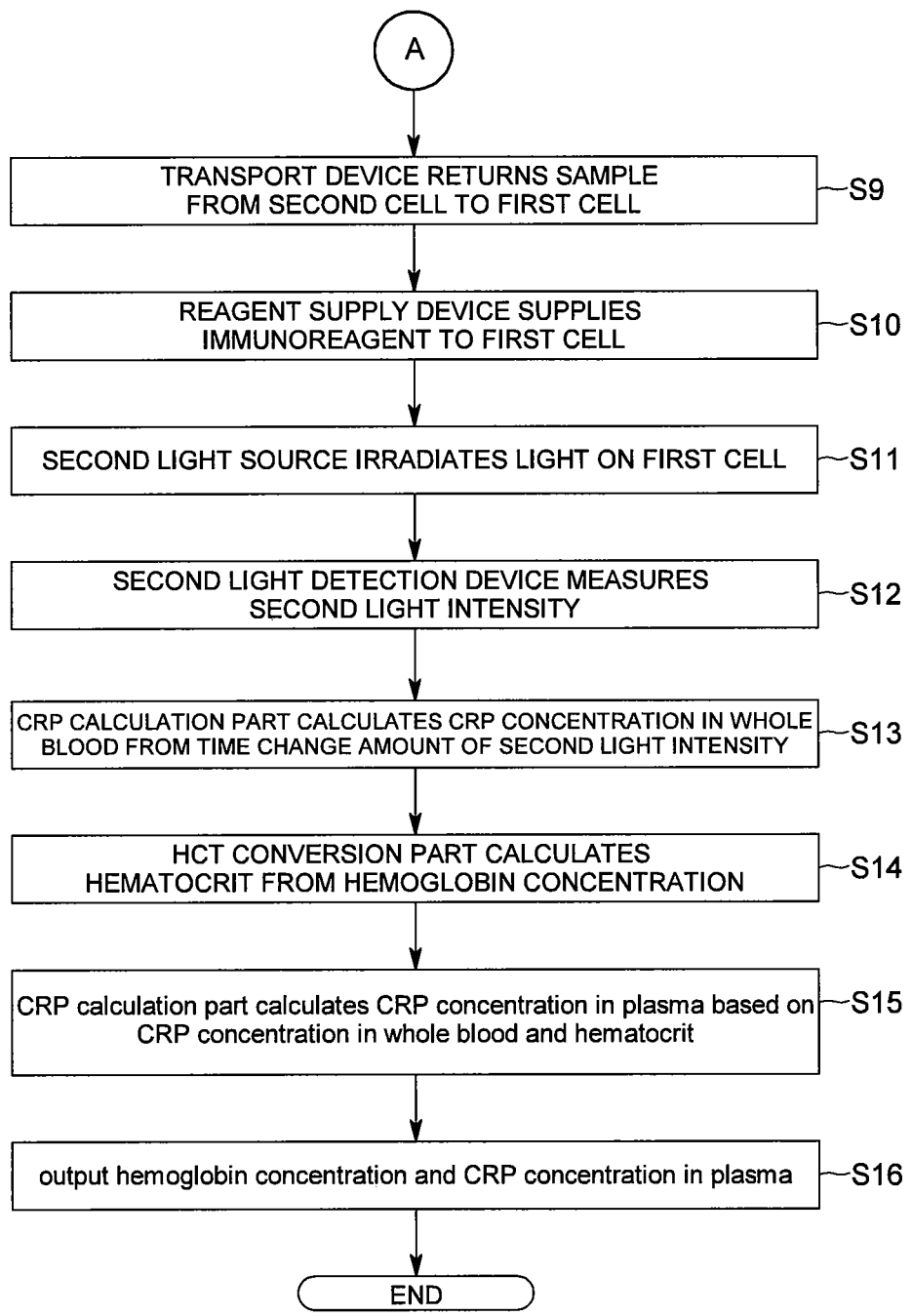
FIG. 4 is a flow chart showing an operation procedure of the whole blood immunity measuring device in accordance with this embodiment.

Next, an operation procedure of the whole blood immunity measuring device 100 will be explained with reference to FIG. 3 and FIG. 4, combined with a detailed explanation of each component of the calculation mechanism 120.

First, when a measurement start switch is on in a state that the blood collection vessel is put close to the whole blood sample collection nozzle so that a distal end of the whole blood sample collection nozzle is immersed in the whole blood sample in the blood collection vessel (step S1), the whole blood sample collection nozzle supplies the whole blood sample to the first cell 10 (step S2). Next, the reagent supply device 40 adds the hemolytic reagent to the whole blood sample housed in the first cell 10 and prepares the first sample (step S3). And then, the reagent supply device 40 adds the buffer reagent to the first sample (step S4).

Furthermore, the transport device 90 introduces the first sample to which the buffer reagent is added and that is housed in the first cell 10 to the second cell 60 (step S5). The first light source 70 irradiates the light on the first sample as being the whole blood sample to which the hemolytic reagent is added and that is housed in the second cell 60 (step S6), and the first light detection device 80 measures the first light intensity as being the intensity of the light transmitting the first sample (step S7). The Hgb calculation part 51 calculates the concentration of hemoglobin in the whole blood based on the first light intensity (step S8).

The transport device 90 returns the first sample housed in the second cell 60 to the first cell 10 (step S9). The reagent supply device 40 adds the immunoreagent to the first sample (step S10). At this time, the agglutination reaction proceeds by the immune reaction of the CRT in the first sample to which the immunoreagent is added and the immunity component in the immunoreagent. During a process of the agglutination reaction, the second light source 20 irradiates the light on the second sample as being the first sample to which the immunoreagent is added and that is housed in the first cell 10 (step S11), the second light detection device 30 measures the second light intensity as being the intensity of the light transmitting the second sample at every predetermined time (step S12).

The CRP calculation part 50 calculates the time change amount of the second light intensity based on each of the second light intensities and calculates the concentration of CRP in the whole blood from the time change amount (step S13). Meanwhile, the Hct conversion part 52 converts the concentration of hemoglobin calculated by the Hgb calculation part 51 into the hematocrit by the use of the previously determined conversion formula (step S14). Next, the CRP calculation part 50 calculates the concentration of CRP in the plasma component based on the concentration of CRP in the whole blood and the hematocrit (step S15), and outputs the concentration of CRP to an output device such as a printer (not shown in drawings) (step S16).

Figure 5:
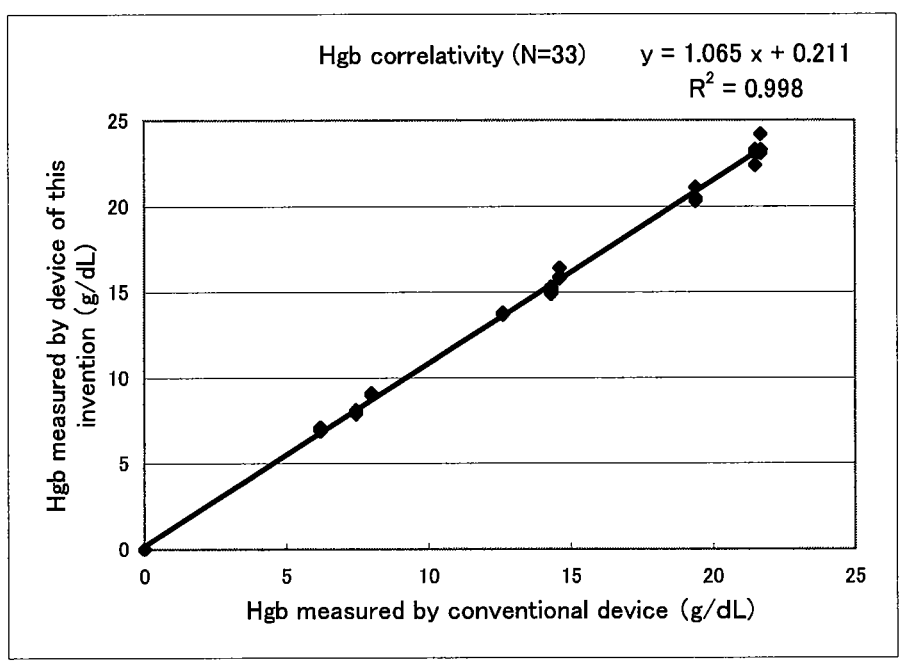
FIG. 5 is a graph showing a concentration of hemoglobin measured by the use of the whole blood immunity measuring device in accordance with this embodiment.

A graph showing correlativity between the concentration of hemoglobin measured by the whole blood immunity measuring device 100 in accordance with this embodiment and the concentration of hemoglobin measured by a conventional device is shown in FIG. 5. This graph makes it clear that each concentration has enough correlativity, and the method for measuring the hemoglobin concentration in accordance with this embodiment is sufficiently accurate.

In accordance with this embodiment, since the concentration of hemoglobin is measured by the use of the first sample as being a product of a previous step of the second sample to be used for measuring the concentration of CRP, it is possible to reduce a number of times to supply the reagent and a number of times to clean the nozzle used for supplying the reagent. As a result of this, it is possible to shorten the time required for measurement and to save a lot of labor. In addition, since there is no need of securing more than a certain amount of the sample for measuring hemoglobin and more than a certain amount of the sample for measuring CRP respectively, it is possible to reduce a necessary amount of the reagent with the measurement accuracy guaranteed so that the running cost can be decreased. In addition, since the amount of the blood to be collected can be decreased, it is also possible to reduce a burden for subject whose blood is collected.

In addition, in case of supplying the whole blood sample to the first cell 10, since all required to do is just to contact the whole blood in the blood collection vessel with the whole blood collection nozzle, it is possible to omit a holder or the like to hold the blood collection vessel.

Furthermore, for the measurement using the whole blood, it is necessary to use the hematocrit to calculate the concentration of CRP in the plasma component. Conventionally, since the hematocrit is calculated by the electric resistance method, electrodes are required, thereby increasing the manufacturing cost. Contrary, due to the keen examination by the inventor of this invention, the inventor has found that it is possible to convert the concentration of hemoglobin into the hematocrit with high accuracy. Since this conversion is used for the whole blood immunity measuring device of this embodiment, it is possible to omit the electrodes, resulting in reducing the manufacturing cost.

The present claimed invention is not limited to the above-mentioned embodiment. For example, the hematocrit is calculated from the concentration of hemoglobin and the concentration of CRP in the plasma component is calculated based on the hematocrit and the concentration of CRP hi the whole blood, however, the concentration of CRP in the plasma component may be calculated based on the concentration of hemoglobin and the concentration of CRP in the whole blood without a process of calculating the hematocrit. In addition, the concentration of CRP in the plasma component may be calculated based on the first light intensity and the second light intensity without calculating the concentration of hemoglobin. Furthermore, in the above-mentioned embodiment, CRP is represented as one example of the measuring object, however, the measuring object may be other substance as far as it can be measured by the immunity measurement. For example, the measuring object may be the substance containing theophylline, cholesterol, hemoglobin A1C, rheumatoid factor, antistreptolysin O(ASO), drug in the blood, and hemolytic streptococcus. In accordance with the whole blood immunity measuring device of this invention, it is possible to calculate the concentration of the measuring object in the plasma component or in the blood cell component from one whole blood sample.

A third cell may be arranged in addition to the first cell and the second cell, and the transport device may transport the sample from the third cell to the second cell and the transport device may transport the sample from the second cell to the first cell.

Furthermore, the reagent supply device may supply each reagent to the first cell by a single reagent supply nozzle, or the reagent supply device may have a plurality of reagent supply nozzles each of which corresponds to each reagent and may supply each reagent by the corresponding reagent supply nozzle. In addition, the hemolytic reagent supply device, the buffer reagent supply device and the immunoreagent supply device are integrally arranged, however, they may be arranged separately.

In addition, the first light source and the second light source are LEDs, however, either one of them or both of them may be a light source device comprising a light source that irradiates the continuous spectrum light such as a xenon lamp and an optical filter that transmits only the light in a predetermined wavelength range and that shields the light in the other wavelength range. In addition, the present claimed invention may be variously modified without departing from a spirit of the invention.

EXPLANATION OF CODES

100 . . . whole blood immunity measuring device
10 . . . first cell
20 . . . second light source
30 . . . second light detection device
40 . . . reagent supply device (hemolytic reagent supply device and immunoreagent supply device)
60 . . . second cell
70 . . . first light source
80 . . . first light detection device
90 . . . transport device
L . . . optical axis direction of light from first light source
F . . . direction of flow

The invention claimed is:

1. A whole blood immunity measuring device comprising a hemolytic reagent supply device configured to supply a hemolytic reagent to a whole blood sample,
a first light source configured to irradiate light on a first sample as being the whole blood sample to which the hemolytic reagent is added,
a first light detection device configured to receive the light emitted from the first light source and transmitting through the first sample and to detect first light intensity as being intensity of the received light,
a Hemoglobin (Hgb) calculation part configured to calculate a hemoglobin concentration in the whole blood sample based on the first light intensity detected by the first light detection device,
an immunoreagent supply device configured to supply an immunoreagent to the first sample,
a second light source configured to irradiate light on a second sample as being the first sample to which the immunoreagent is added,
a second light detection device configured to receive the light emitted from the second light source and transmitting through the second sample and to detect second light intensity as being intensity of the received light, and a measuring object calculation part configured to calculate a concentration of the measuring object based on the second light intensity in the process of an immune reaction of the measuring object to the immune component in the immunoreagent after the immunoreagent is added by the immunoreagent supply device and the concentration of hemoglobin calculated by the Hgb calculation part.

2. The whole blood immunity measuring device described in claim 1, further comprising
a first cell, a second cell arranged separately from the first cell and a transport device configured to transport the first sample between the first cell and the second cell, wherein
the first light source irradiates the light on the first sample transported to the second cell from the first cell by the transport device,
the immunoreagent supply device supplies the immunoreagent to the first sample returned to the first cell from the second cell by the transport device, and
the second light source irradiates the light on the second sample housed in the first cell.

3. The whole blood immunity measuring device described in claim 2, wherein
an internal flow channel formed inside of the second cell is in a shape of getting thicker smoothly and gradually from an introducing port from which the first sample is introduced and a lead-out port from which the sample is lead out headed to a center part viewed from an optical axis direction of the light from the first light source.

4. The whole blood immunity measuring device described in claim 3, wherein
a width in a direction orthogonal both to the direction of the flow of the sample and to a direction of an optical axis of the light from the first light source in the center part of the internal flow channel of the second cell is 1.2~2.0 times as long as a width in the orthogonal direction in the introducing port and the lead-out port.

5. The whole blood immunity measuring device described in claim 1, wherein
the measuring object is C-reactive protein.

6. A whole blood immunity measuring method comprising;
preparing a first sample by adding a hemolytic reagent to whole blood,
irradiating light on the first sample and measuring first light intensity as being intensity of transmitting through the first sample,
calculating a concentration of hemoglobin in the whole blood based on the first light intensity,
adding the immunoreagent to the first sample and causing an immune reaction of a measuring object in the first sample to an immune component in the immunoreagent,
irradiating light on a second sample as being the first sample to which the immunoreagent is added and measuring the second light intensity as being the intensity of the light transmitting through the second sample in the process of an immune reaction of the measuring object to the immune component, and
calculating a concentration of the measuring object based on the second light intensity and the hemoglobin concentration.

* * * * *